United States Patent [19]
Ottesen et al.

[11] Patent Number: 5,984,998
[45] Date of Patent: Nov. 16, 1999

[54] METHOD AND APPARATUS FOR OFF-GAS COMPOSITION SENSING

[75] Inventors: David Keith Ottesen, Livermore; Sarah Williams Allendorf, Fremont; Gary Lee Hubbard, Richmond, all of Calif.; David Ezechiel Rosenberg, Columbia, Md.

[73] Assignee: American Iron and Steel Institute, Washington, D.C.

[21] Appl. No.: 08/970,826

[22] Filed: Nov. 14, 1997

[51] Int. Cl.$^6$ .................................................. C21C 1/04
[52] U.S. Cl. ................... 75/375; 266/80; 266/99
[58] Field of Search ................ 75/375; 266/80, 266/99, 78

[56] References Cited

U.S. PATENT DOCUMENTS

| | | | |
|---|---|---|---|
| 3,561,743 | 2/1971 | Schroeder et al. | 266/35 |
| 3,652,262 | 3/1972 | Denis | 75/60 |
| 3,720,404 | 3/1973 | Carlson et al. | 266/34 R |
| 3,831,030 | 8/1974 | Wrobel et al. | 250/339 |
| 3,871,871 | 3/1975 | Denis et al. | 75/60 |
| 3,920,447 | 11/1975 | Schroeder et al. | 75/60 |
| 4,043,801 | 8/1977 | Sakamoto et al. | 75/60 |
| 4,232,852 | 11/1980 | Limque et al. | 266/80 |
| 4,410,273 | 10/1983 | Mantz et al. | 356/319 |
| 4,474,361 | 10/1984 | Kanemoto et al. | 266/96 |
| 5,026,991 | 6/1991 | Goldstein et al. | 250/343 |
| 5,173,749 | 12/1992 | Tell et al. | 356/437 |
| 5,246,482 | 9/1993 | Murakami et al. | 75/378 |
| 5,331,409 | 7/1994 | Thurtell et al. | 356/437 |
| 5,603,746 | 2/1997 | Sharan | 75/375 |

FOREIGN PATENT DOCUMENTS

| | | |
|---|---|---|
| 0768525 | 4/1997 | European Pat. Off. . |
| 61-201713 | 9/1986 | Japan . |
| 870443 | 10/1981 | U.S.S.R. . |
| 1497229 | 7/1989 | U.S.S.R. . |
| 2116316 | 9/1983 | United Kingdom . |
| WO86/07455 | 12/1986 | WIPO . |
| WO91/04470 | 4/1991 | WIPO . |
| WO92/02824 | 2/1992 | WIPO . |

*Primary Examiner*—Scott Kastler
*Attorney, Agent, or Firm*—Fitzpatrick, Cella, Harper & Scinto

[57] ABSTRACT

An apparatus and method for non-intrusive collection of off-gas data in a steelmaking furnace includes structure and steps for transmitting a laser beam through the off-gas produced by a steelmaking furnace, for controlling the transmitting to repeatedly scan the laser beam through a plurality of wavelengths in its tuning range, and for detecting the laser beam transmitted through the off-gas and converting the detected laser beam to an electrical signal. The electrical signal is processed to determine characteristics of the off-gas that are used to analyze and/or control the steelmaking process.

32 Claims, 13 Drawing Sheets

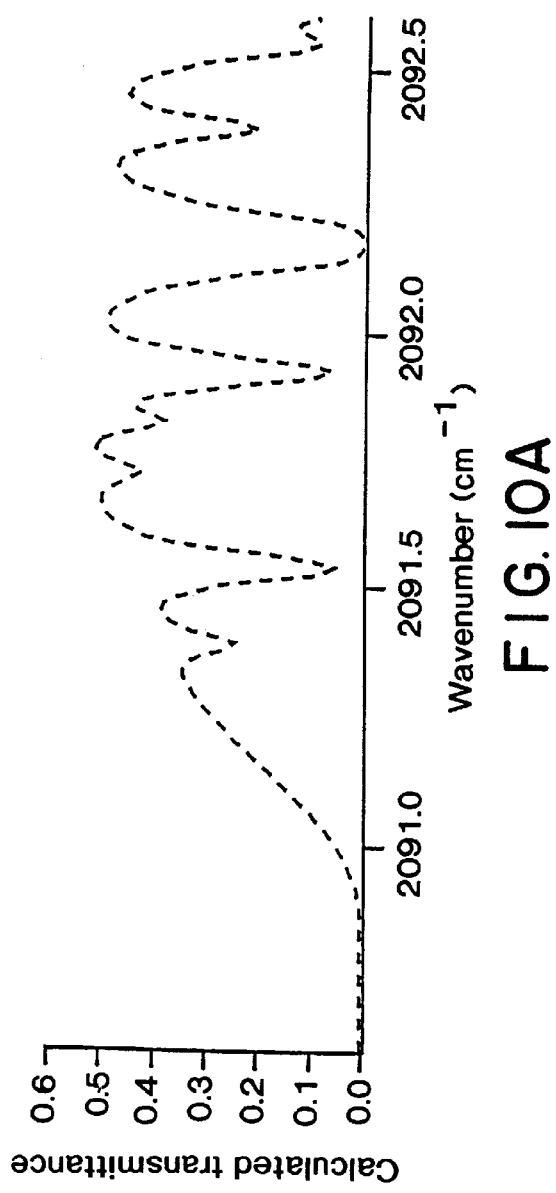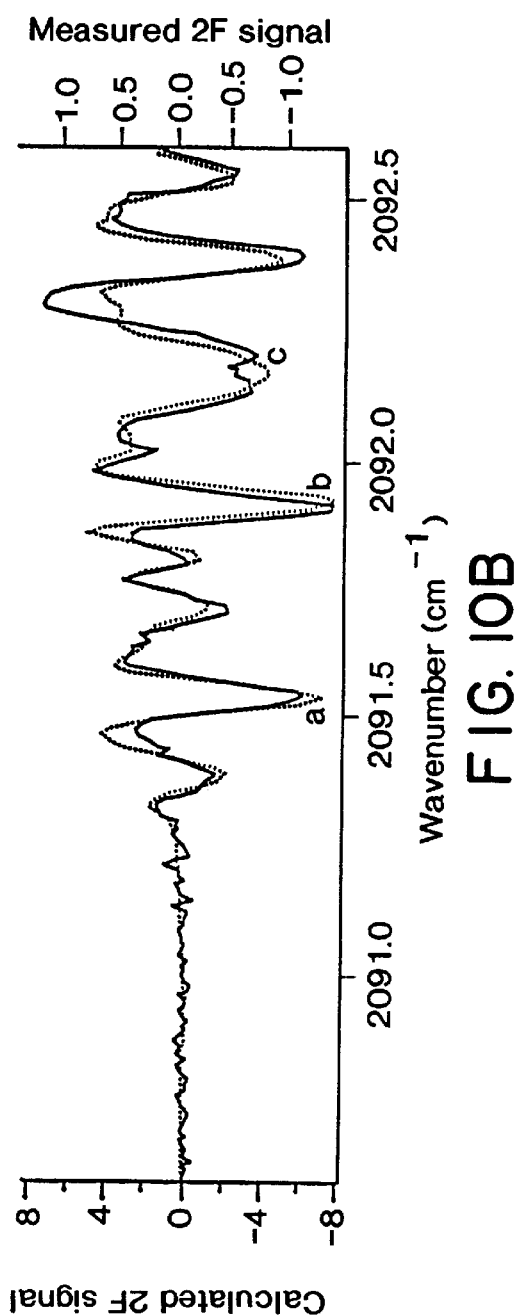

METHOD AND APPARATUS FOR OFF-GAS COMPOSITION SENSING

NOTICE OF GOVERNMENT INTEREST

The Government of the United States of America has rights in this invention pursuant to Cooperative Agreement No. DE-FC07-93ID13205 awarded by the U.S. Department of Energy.

FIELD OF THE INVENTION

The present invention relates generally to improvements in steelmaking, and more particularly to improvements in measuring dynamic process characteristics in a steelmaking process.

BACKGROUND OF THE INVENTION

Conventional control technology in the steelmaking industry relies on static computer models, e.g., feed-forward heat and material balance computer models. The composition and weight of starting materials (e.g., pig iron, scrap steel, oxygen, fluxes, etc.) are input to the model, and oxygen flow rate and blowing time are calculated by the model. Due to the unknown composition of the scrap steel, significant inaccuracies occur in achieving the desired endpoint concentration of carbon and melt temperature in the final steel product. However, no practical real-time method is conventionally available for monitoring process characteristics of the steelmaking process, and therefore no dynamic control of a process can be performed.

The unavailability of real-time process monitoring and dynamic process control causes significant safety and efficiency problems for current steelmaking processes, such as the basic oxygen process. This process combusts oxygen with carbon contained in molten metal to transform the molten metal to steel. Safe and efficient transformation requires that process variables be controlled to maintain certain process characteristics (e.g., temperature and concentrations of CO, $CO_2$, and $H_2O$) at preferred or optimum values. Since there presently is no on-line, real-time method to measure or monitor these process characteristics, dynamic adjustments cannot be made to ensure maximum safety and efficiency.

More particularly, current commercial methods for producing steel using the basic oxygen process involve transforming starting materials containing a relatively high carbon content (up to about 4 wt %) by blowing high velocity oxygen into the starting materials in a batch process called a "heat." The oxygen combusts with carbon contained in the starting materials to decrease the carbon content, resulting in steel containing carbon at levels of 0.03 to 0.6 wt %, depending on the desired alloy. The starting materials include molten metal and flux (collectively referred to as the "bath"), and during the steelmaking process they form both melt and slag phases in a furnace.

The process is carried out in a basic oxygen furnace (BOF), which includes a large vessel with a refractory lining for containing the bath, an oxygen lance for blowing oxygen into the bath, and exhaust ducts for removing gases produced by the steelmaking process. These gases are collectively referred to as the off-gas. One of the principal gases produced by the process is carbon monoxide (CO)—the primary reaction product of oxygen and carbon. A variety of schemes exist to further react this CO with oxygen prior to its exit from the furnace, to form carbon dioxide ($CO_2$). This post-combustion reaction of CO and oxygen is highly exothermic, and therefore it releases heat to both the slag and the melt phases in the furnace. This additional heat accelerates the steel conversion process.

A significant problem with commercial steelmaking is making efficient use of the CO, i.e., efficiently controlling post-combustion of CO, which requires proper control of the oxygen flow rate. If insufficient oxygen is injected, then the maximum effective use of CO is not achieved. On the other hand, if too much oxygen is injected, then the process is not cost effective because oxygen is wasted and the off-gas becomes too hot, deleteriously affecting the refractory lining and the exhaust duct walls. Conventionally, post-combustion of CO is monitored in a time-averaged fashion using commercially-available mass spectrometry (MS) or non-dispersive infrared absorption (NDIR) methods. These methods require that a sample of the off-gas be extracted, cooled, and analyzed, and therefore there is a significant time delay in acquiring data. Some indication of post-combustion gas concentrations may also be derived by monitoring wall and cooling water temperatures in the exhaust ducting using standard thermocouple technology. However, this technique is severely limited in sensitivity, accuracy, and response time. This lack of on-line, real-time measurement of CO and $CO_2$ concentrations in the off-gas prevents efficient control of the oxygen flow rate in conventional steelmaking processes to ensure optimal post-combustion of CO.

Another major problem with current commercial steelmaking methods is the lack of an on-line method to provide continuous, real-time data on the carbon content of the metal. In many commercial steel mills, the carbon endpoint concentration is determined by stopping the process at the predicted endpoint, extracting a sample of the molten steel, and performing an offline chemical analysis. Another technique involves using "sensor lance" technology, which requires the lowering of a water-cooled lance equipped with an expendable sensor into the furnace. The expendable sensor is immersed in the liquid steel near the predicted endpoint of oxygen blowing, a metal sample is extracted, and the cooling curve of the sample is measured. This cooling curve can then be related to the carbon concentration of the steel. Both of these methods yield only a single data point per heat rather than continuous data.

Other methods for carbon endpoint verification use MS or NDIR absorption methods to determine CO and $CO_2$ concentrations in the exhaust gas after it has been cooled and particulates have been removed. These methods require the use of an off-gas treatment system to treat the gas, and such a system requires extensive maintenance.

As a result of the lack of continuous data, steelmakers sometimes resort to a technique in which a heat is "blown flat" to ensure that the molten metal has been adequately decarburized. The "blown flat" technique uses excess oxygen to reduce the carbon concentration in the melt down to the lower limit of the desired range, i.e., 0.03 wt %. After the vessel is tapped and the steel is transferred to a ladle, the carbon concentration is adjusted back up to the desired level by adding material in the ladle.

However, this process is inefficient for several reasons. First, excess oxygen is used to ensure the complete oxidation of carbon in the melt, necessitating an additional expense. Second, the use of excess oxygen causes iron in the molten bath to begin to oxidize when the dissolved carbon has been reduced to very low concentrations. This oxidation results in a loss of iron, which should form a portion of the commercial product, to iron oxide that ends up in the slag phase.

Finally, the process of blowing flat requires the expenditure of unnecessary additional processing time, thereby reducing throughput in the industrial process and consequently increasing costs and lowering profits.

Another significant problem with current steelmaking methods is the creation of a highly reactive, foaming slag layer when certain combinations of hot metal chemistry and flux additions are used, which causes ejection of large amounts of liquid slag from the BOF vessel during oxygen blowing (referred to as "slopping"). This slopping causes undesirable rapid slag build-up on the vessel mouth and exhaust hood surfaces, and increased skull build-up on the lance. Slopping can be controlled by adjusting the lance parameters (e.g., the lance height above the bath and the oxygen flow rate), but this is difficult to achieve automatically, since current steelmaking techniques cannot detect the amount of liquid slag being ejected from the furnace.

Yet another significant difficulty with current steelmaking methods results from the presence of a large amount of water in the furnace. A large amount of water in the furnace causes rapid formation of molecular hydrogen at the melt surface, thereby creating a major safety hazard due to the risk of an explosion. The presence of excess water may be caused by unwanted leaks of cooling water from a water-cooled oxygen lance or water-cooled off-gas exhaust ducts. Conventionally, the potential for hydrogen formation in the steel conversion furnace is determined by monitoring input and output cooling water flows through the oxygen lance and an exhaust hood system. Large discrepancies or sudden changes in flow rates could indicate dangerous leaks into the furnace vessel. However, while water flow monitoring may indicate the source of water that may cause dangerous levels of hydrogen, this method does not indicate the levels of hydrogen actually present, and therefore this method fails to offer adequate safeguards against explosions.

In an effort to address the above-noted limitations of conventional monitoring techniques, research has been conducted on methods for sampling gas near the furnace mouth using water-cooled extractive probes. The extracted gas is then analyzed, either with Fourier transform infrared (FTIR) spectroscopy or mass spectrometry. The FTIR method provides a relatively real-time response for measuring gas-phase concentration, as compared with the methods described above. However, an extractive probe has a limited life due to its location above the furnace mouth. Further, the off-gas temperature is measured in this technique by a thermocouple located in the extraction probe, and such thermocouples have slow response times.

Accordingly, an improved monitoring method is needed that can provide real-time, continuous data about off-gas characteristics using a reliable, non-intrusive method.

SUMMARY OF THE INVENTION

An object of the present invention is to provide an improved method and apparatus for monitoring dynamic process characteristics in a manufacturing process. In particular, an object of the invention is to provide a non-intrusive method for obtaining real-time data about off-gas characteristics to permit analysis and/or dynamic control of a steelmaking process.

According to a first preferred embodiment of the invention, means (or a step) for transmitting a laser beam through the off-gas produced by a steelmaking furnace is provided, which has a tuning range of laser beam wavelengths. Means (or a step) for controlling the transmitting to repeatedly scan the laser beam through a plurality of wavelengths in its tuning range is also provided, together with means (or a step) for detecting the laser beam transmitted through the off-gas and for converting the detected laser beam to an electrical signal.

According to another preferred embodiment, means or steps are provided for transmitting a laser beam through the off-gas of the steelmaking furnace, the laser beam being repeatedly scanned through a range of wavelengths during transmission, for detecting the transmitted laser beam, for generating an electrical signal corresponding to the detected laser beam, and for processing the electrical signal to determine at least one characteristic of the off-gas in the steelmaking furnace.

According to yet another preferred embodiment, an apparatus for non-intrusive collection of off-gas data in a steelmaking furnace is provided that comprises a tunable diode laser arranged to transmit a laser beam through the off-gas produced by the steelmaking furnace, a control circuit electrically connected to the tunable diode laser to provide an injection current to the tunable diode laser, the control circuit varying the injection current provided to the laser so that the laser outputs a laser beam whose wavelength is repeatedly scanned through a plurality of wavelengths, and a detector that receives the laser beam and generates an electrical signal corresponding to the received laser beam. The apparatus may also include a computer that receives and processes the electrical signal to determine at least one characteristic of the off-gas. Further, the control circuit may be constructed to vary the injection current to wavelength modulate the laser beam while scanning the laser beam through the plurality of wavelengths, and the detector may include a lock-in amplifier for detecting a harmonic signal of the modulated laser beam.

Further objects and aspects of the present invention will be apparent to those of ordinary skill from the detailed description of the preferred embodiments, which are discussed below with reference to the attached drawings.

BRIEF DESCRIPTION OF THE DRAWINGS

FIG. 9b is a graph of the experimentally measured second harmonic spectrum and a calculated second harmonic spectrum of the spectrum in FIG. 9a.

FIG. 10a is a graph showing calculated transmittance values as a function of wavenumber.

FIG. 10b is a graph showing calculated second harmonic transmittance values calculated from the graph of transmittance values shown in FIG. 10a, and also showing measured second harmonic transmittance values.

DESCRIPTION OF THE PREFERRED EMBODIMENT

The present invention is a non-intrusive, optical sensor system. This system monitors the dynamic process characteristics of a steelmaking process by measuring characteristics of the off-gas produced by a steelmaking furnace. This is accomplished by transmitting a tunable diode laser beam through the off-gas while scanning the laser beam through a range of wavelengths, and detecting the beam with an infrared optical detector module. The resulting signal is then processed to analyze laser transmittance and absorption intensities that indicate process characteristics, such as CO and $CO_2$ concentrations, temperature, carbon endpoint level (i.e., carbon content), furnace slopping, and water vapor concentration.

Generally, an optical sensor system according to the present invention comprises four distinct sections: (1) a tunable laser source (with an associated electronics module), (2) a detector module, (3) an optical path from the laser source to the detector module, which passes through the off-gas produced by a steelmaking furnace, e.g., a basic oxygen furnace (BOF), and (4) a data acquisition/display/output module.

The structure of a preferred embodiment of the present invention is described with respect to FIGS. 1 through 4, followed by a description of the operation of the preferred embodiment. Although the preferred embodiment is described with reference to a basic oxygen furnace, the invention is not limited to such an application. Rather, the invention is generally applicable to analysis of off-gas streams, and to the control of steelmaking processes, in which an optical line-of-sight can be made available for laser beam transmission. In addition to basic oxygen furnaces, other examples include electric arc furnaces and bottom-blown oxygen furnaces.

Figure 1:
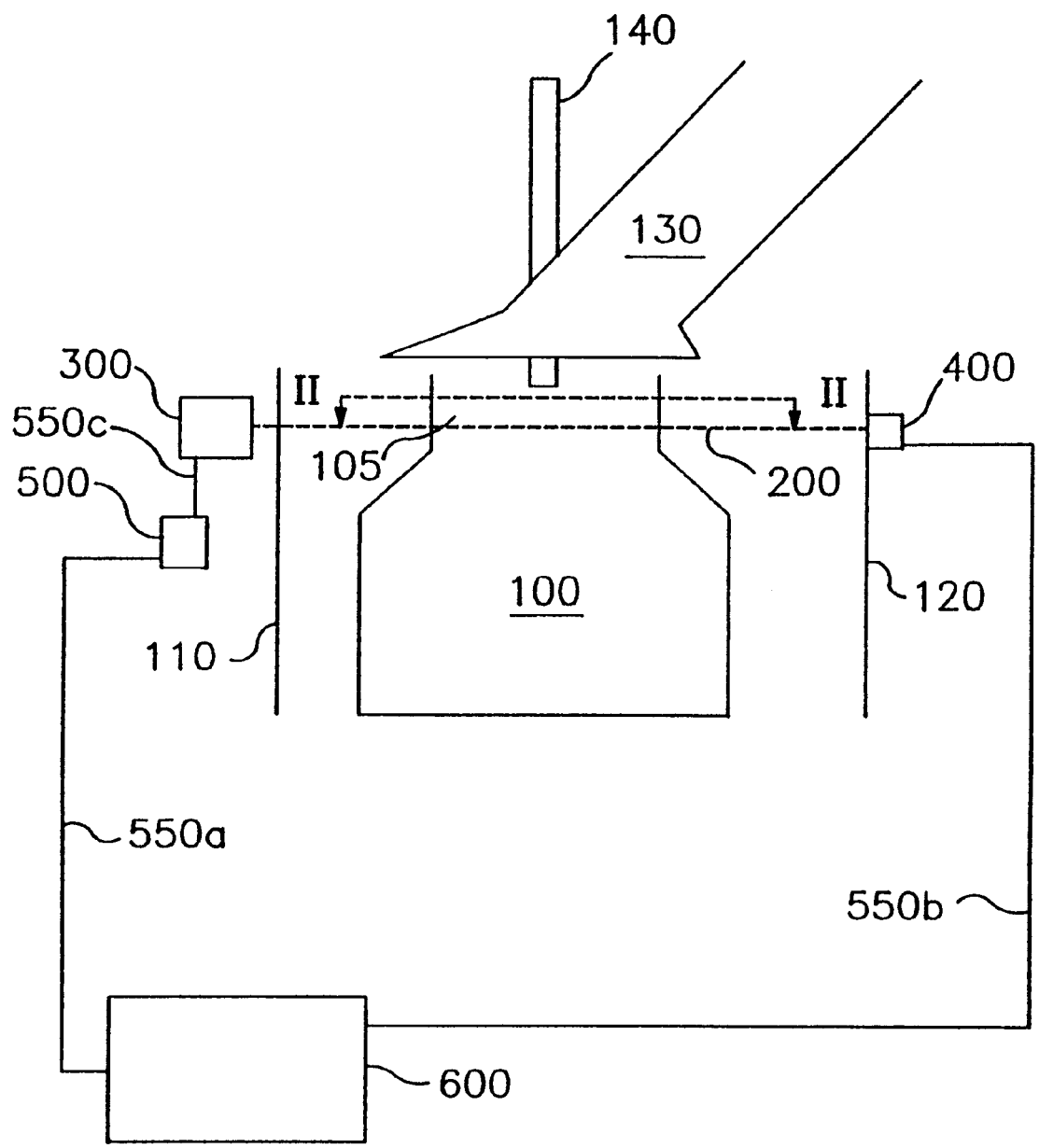
FIG. 1 is a schematic view showing a configuration of the present invention suitable for a basic oxygen furnace.

FIG. 1 shows a deployment of the invention suitable for a basic oxygen furnace 100 having a mouth 105. The furnace is surrounded by heat shields 110 and 120. An exhaust hood 130 is positioned close to the mouth 105 of furnace 100 (e.g., separated by a gap of about 3 feet) to collect the off-gas. A vertically adjustable oxygen lance 140 is insertable into the furnace 100 to inject oxygen into the furnace.

As shown in FIG. 1, an optical path 200 located just above the furnace mouth links a tunable laser source 300 and an infrared signal detector module 400, which are respectively mounted behind heat shields 110 and 120 at opposite sides of furnace 100. Holes are provided in heat shields 110 and 120 to provide a laser beam path between laser source 300 and detector module 400. In the preferred embodiment these holes have a diameter of about 3 inches, but the size is not critical. An electronics module 500 is disposed on the side of heat shield 110 adjacent the laser source 300. Laser source 300 and electronics module 500 are interconnected by appropriate electrical cables 550c, and detector module 400 and electronics module 500 are connected by electrical cables 550b and 550a, respectively, to a data acquisition/display/output module 600 that is remotely located.

Figure 2:
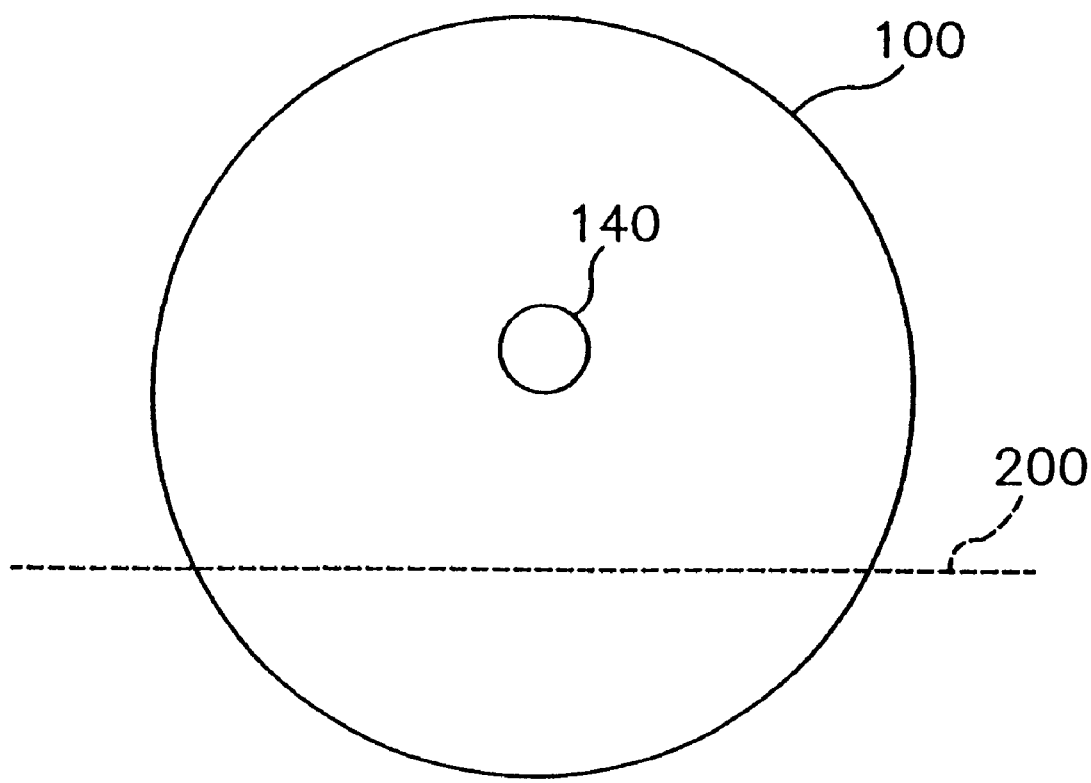
FIG. 2 is a cross-sectional view of the basic oxygen furnace shown in FIG. 1 taken along line II—II.

FIG. 2 is a cross-sectional view of furnace 100 taken along sectional line II—II shown in FIG. 1. As shown in FIG. 2, optical path 200 is offset from the center of the furnace to one side of oxygen lance 140.

Figure 3:
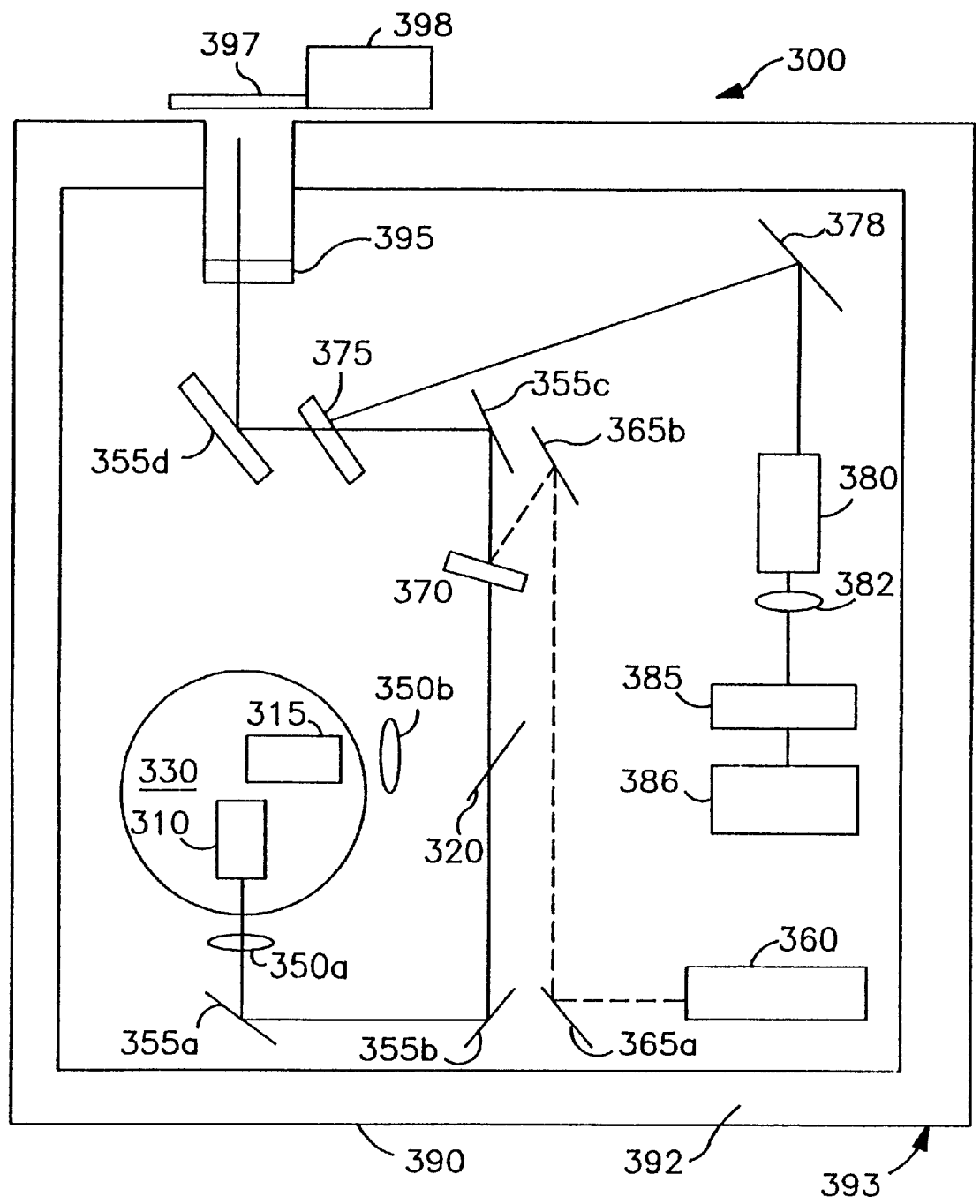
FIG. 3 is a schematic view showing the components of a laser source module.
Figure 4:
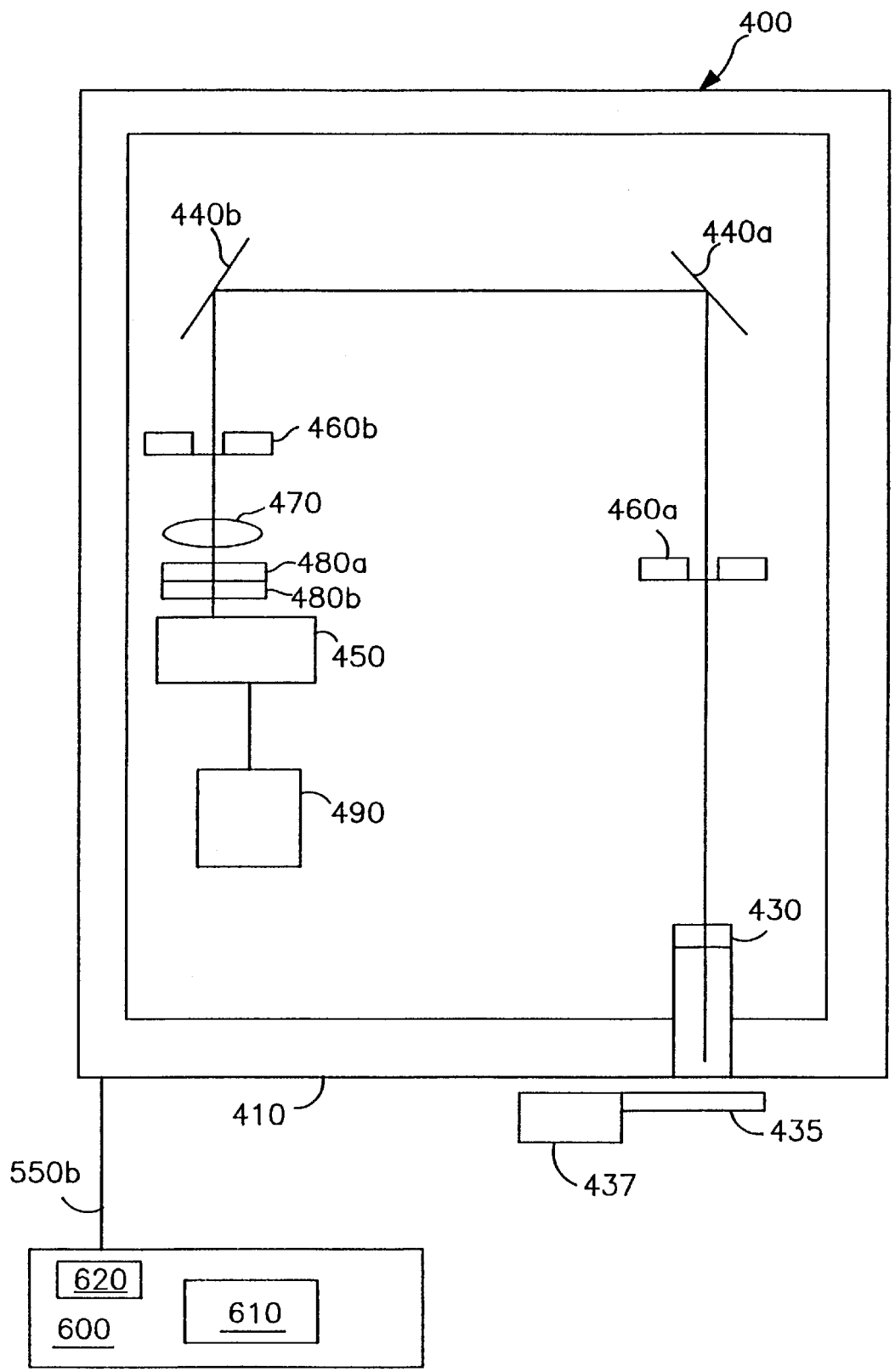
FIG. 4 is a schematic view showing the components of a detector module.

Additional details of the laser source, the detector module, and the data acquisition/display/output system are discussed with respect to FIGS. 3 and 4.

As shown in FIG. 3, the laser source 300 includes two tunable infrared lasers 310 and 315. Lasers 310 and 315 are similar in their electrical and optical characteristics. Laser 310 is actively used in off-gas measurements while laser 315 is reserved as a spare. The laser to be used is selected by computer control (discussed below with respect to electronics module 500), and the beam path is determined by the presence or absence of a removable mirror 320. In the preferred embodiment, each of lasers 310 and 315 is capable of at least 0.01 $cm^{-1}$ spectral resolution at a wavenumber of 1900 to 2200 $cm^{-1}$ (4.55 to 5.26 $\mu$m). In operation, the laser that is used is configured to work in a tuning range that is narrower than its possible operating range, for example, 2111 to 2115 $cm^{-1}$. In addition, by selecting the optimal tuning range for other types of steelmaking processes or for determining off-gas characteristics other than those discussed below, the preferred embodiment can be adapted for use in such other types of steelmaking processes or for determining other off-gas characteristics. Accordingly, lasers capable of operating in the broader range of 1700 to 2500 $cm^{-1}$ (4.00 to 5.88 $\mu$m) may be used to provide greater flexibility in selecting an appropriate tuning range.

In the preferred embodiment, lasers 310 and 315 are commercially-available lead-salt-diode semiconductor lasers that emit extremely narrow linewidth radiation (0.0005 $cm^{-1}$) in the mid-infrared region, such as a Model L5621 laser, manufactured by Laser Photonics Inc., Andover, Mass. These lasers are continuously tunable over a range of about 2 to 4 $cm^{-1}$ by adjusting the diode injection current. They are non-hazardous, Class 1 lasers.

Associated with the lasers is an evacuable dewar housing 330 capable of being cooled down to the temperature of liquid nitrogen. The laser outputs from the dewar housing 330 are diverging infrared beams, and therefore a lens (350a, 350b) is provided in each beam path to collimate the respective beam. Lenses 350a and 350b are f/1, 1.5-inch focal length, calcium-fluoride lenses. Mirrors 355a, 355b, 355c, and 355d are also provided for directing the laser beam, with mirror 355d being a remotely operated mirror that is adjustable to alter the position of the beam path through the furnace off-gas. A solid line in FIG. 3 from laser 310 illustrates the tunable diode laser (TDL) beam path.

Since the TDL lases at an infrared wavelength and therefore is invisible, a visible alignment beam is transmitted along the TDL line-of-sight to aid in fast and accurate alignment of the TDL beam with the detector module during sensor installation. The alignment beam is generated by a visible alignment laser 360 and is guided by mirrors 365a and 365b to the second surface of a narrow-band optical filter 370 in the TDL beam path. The infrared TDL beam and the visible laser beam are combined on the second surface of filter 370 to produce stable, precisely collinear beams. A dashed line in FIG. 3 illustrates the visible laser beam path from the laser 360 up to the beam-combining filter 370.

As shown in FIG. 3, a reference beam is provided by inserting a calcium fluoride window 375 into the TDL beam to serve as a beamsplitter. Window 375 directs approximately 5 to 10% of the incident laser beam power, via a mirror 378, through a gas cell 380 filled with low pressure CO (about 40 torr). The beam exiting gas cell 380 is focused by a calcium fluoride lens 382 onto an indium-antimonide (InSb), or other suitable material, infrared reference-detector 385, which outputs a detection signal that is amplified by an amplifier 386. A characteristic absorption pattern of narrow absorption lines is produced as the TDL is scanned through its injection-current tuning range. This distinctive pattern is used to verify that the temperature tuning of the diode laser is set correctly and that the desired diode-current tuning-range is being scanned.

The components of the laser source 300 are enclosed in an enclosure 390 to provide for appropriate environmental control. Enclosure 390 is hermetically sealed to prevent the intrusion of dust into the enclosure. The enclosure consists of a double-walled water jacket 392 for cooling purposes, with additional thermal insulation 393 mounted on the outside. The internal components of the laser source 300 are additionally cooled by a stream of cool, dry air by a mechanism (not shown) that creates a positive pressure within the enclosure. Both the cooling water and cool, dry air are supplied by utilities in the steelmaking plant.

Enclosure 390 has a window 395 composed of calcium fluoride, or some other suitable infrared-transmitting material, mounted in one wall to permit egress of the TDL beam. Window 395 is anti-reflection coated for the wavelength range in which the TDL is operated, to prevent the formation of interference fringes ("etalons") in the detected TDL signal. The outer window surface is purged with dry, instrument-air by a mechanism that is not shown to prevent the accumulation of dust and debris on its surface. A motor-driven shutter 397 is provided on the outside of enclosure 390 to protect the surface of window 395 when no measurements are being made. The motor-driven shutter 397 is driven by a motor 398 and can be operated either manually or under computer control.

To provide a stable base, laser source 300 is mounted on a plate (not shown) composed of aluminum or a steel-honeycomb baseplate of sufficient thickness (at least one inch) to provide stability for the mounted optical components within enclosure 390. The baseplate is insulated and firmly mounted on a platform adjacent to the off-gas stream. The mounting platform should be sufficiently rigid to support the laser source 300, and should be protected by heat shields to minimize the radiant and convective heat loads generated by the steelmaking process and the off-gas stream.

Electronics module 500 (shown in FIG. 1) contains standard electronic components necessary to control and stabilize the output of the tunable diode laser. Additional components include power supplies for several components in the laser source 300 (visible diode alignment laser 360, remotely operated mirror 355d, reference detector amplifier 386, and shutter motor 398). These components are remotely controlled by the data acquisition/display/output module 600 to power the laser source components according to the timing of the measurements to be made. The electronics module 500 is cooled and purged by dry air by a mechanism which is not shown. The cables connecting the electronics module 500 to the laser source 300 and data acquisition/display/output module 600 pass through two holes in the electronics module housing. These holes are used as egress for the dry, purge air, as are similar holes in the laser source and detector modules.

As shown in FIG. 1, the laser beam passes through the off-gas in BOF 100, adjacent to oxygen lance 140. Absorption of the laser beam varies as a function of wavenumber, and individual absorption lines that are due solely to vibrationally excited gas-phase molecules in the off-gas can be monitored by detector module 400. In this manner, inaccuracies due to optical absorption caused by CO, $CO_2$, and $H_2O$ molecules outside the hot zone along the optical line-of-sight are avoided when calculating gas concentrations and temperatures. In addition to molecular absorption along the optical path, the laser beam may be severely attenuated in its passage through the off-gas due to scattering caused by the very large number of small particles entrained in the gas flow. This attenuation may necessitate the use of path-shortening devices for some applications. Path-shortening devices may comprise opposable tubes that extend into the off-gas flow a short distance along the line-of-sight of the laser beam. The tubes are purged with a flow of either air or some inert gas, and act to shorten the optical path length through the particle-laden off-gas. Since path-shortening devices contain no optical components, they may be formed from cheap materials and are considered to be disposable items in the event of sudden failure due to slag accretion or impact damage from flying debris.

In addition to absorption and attenuation, additional optical interference at detector module 400 is generated by fluctuating broad-band emissions from particles and gas molecules within the off-gas stream. Further, turbulence within the off-gas stream and large thermal differentials along the optical path cause the transmitted laser beam to be red in a random fashion as it enters detection module 400. Accordingly, a highly-sensitive configuration is required for detection module 400 to adequately detect the very weak transmitted beam.

FIG. 4 shows the structure of a preferred embodiment of infrared signal detector module 400. As shown in FIG. 4, the components of the detector module are housed in a water-jacketed, hermetically-sealed enclosure 410 similar to the enclosure described for the laser source 300. Enclosure 410 provides cooling and environmental control for the components of the detector module. The enclosure is mounted on a baseplate (not shown) similar to that described for the laser source 300, to provide a stable base for the detector module components.

A calcium fluoride window 430 having an anti-reflection coating is provided in a wall of enclosure 410. Window 430 is used to transmit the TDL beam into the detector module while also serving to seal the module against the intrusion of hot gases and dust. As with the calcium fluoride window 395 of the laser source, an anti-reflection coating reduces the formation of etalons in the detected signal, and the outer surface of window 430 is purged with dry instrument air by a mechanism that is not shown, to prevent the accumulation of dust particles on its surface. A shutter 435 driven by a motor 437 is provided to protect window 430 when measurements are not being made.

Mirrors 440a and 440b are provided for guiding the laser beam entering the detector module to an InSb, or other suitable material, detector 450. Detector 450 has a 1 mm diameter detector surface. Two or more apertures 460a, 460b are provided along the line of sight within the detector module to physically block unwanted off-axis light from striking detector 450, as well as decreasing the thermal background and experimental noise level. A fast (i.e., low f-number) calcium-fluoride lens 470 is used to focus the transmitted laser beam onto the detector surface. In the preferred embodiment, a lens having an f-number of 1 is used. This high collection efficiency and resulting small image size reduces signal loss due to steering of the laser beam while it traverses the off-gas. A combination of narrow-band optical filters 480a, 480b is placed immediately before the detector 450 so that the resulting filter bandpass is centered about the optimum laser tuning range. This limits unwanted broad-band light so that only light in the wavenumber range essential for laser detection reaches the detector. For the detector used in the preferred embodiment, and the background conditions existing in the BOF off-gas, a bandpass of no more than 30 cm$^{-1}$ should preferably be used to prevent the detector from overloading, while providing a sufficient transmitted laser signal for a satisfactory dynamic range. An amplifier 490 is provided to amplify the detection signal output by detector 450.

Data acquisition/display/output module 600 includes a data processing computer 610 such as, for example, a PC-based computer control system. Data acquisition/display/output module 600 also includes a 100 KHz lock-in amplifier 620, through which signals from detector module 400 are routed in the harmonic detection operating mode (discussed below). Computer 610 receives absorption spectra from the reference detector 385 (after amplification by amplifier 386) and from the detector 450 (after amplification by amplifier 490 and, in the harmonic detection mode, 100 KHz lock-in amplifier 620), and the computer averages periodic samples of the signal from detector 450 to maximize the system's signal-to-noise ratio. A resulting total response time of one to five seconds per time-averaged measurement is achieved, depending on furnace conditions and the desired signal-to-noise ratio (i.e., averaging more samples over a longer period will improve the signal-to-noise ratio). After processing, the data can be displayed as screen outputs, output to a printer, or used to generate process control signals that are output to sound an alarm that a predetermined condition is met (e.g., hazardous amounts of water have been detected that may cause a build-up of hydrogen resulting in an explosion) or are output to control process parameters (e.g., to vary the rate of oxygen flow in the lance).

The operation of the preferred embodiment will now be discussed with respect to FIGS. 5–13. Two distinct modes of operation are possible—the direct absorption mode and the harmonic detection mode. In the direct absorption mode, a transmitted infrared laser beam is analyzed directly for detecting absorption features due to gas-phase species (e.g., CO, $CO_2$, $H_2O$) in the off-gas, and the results are interpreted in terms of gas temperature and concentrations to permit real-time process control. This mode of operation is particularly appropriate for off-gas streams that are small in diameter and/or possess relatively low dust loading, such that the average maximum transmitted laser power is at least 10% of the original laser power.

In the harmonic detection mode an incident laser beam is modulated (either in amplitude or in wavelength) at a high frequency in addition to being scanned through a wavelength range. The transmitted laser beam is detected and processed using a phase-sensitive device (e.g., lock-in amplifier 620 shown in FIG. 4) at the first or second harmonic frequency of the high-frequency modulation. Absorption features due to gas-phase species (e.g., CO, $CO_2$, $H_2O$) in the off-gas are observed, and the results are interpreted in terms of gas temperature and concentrations to permit real-time process control. This mode of operation is particularly appropriate for off-gas streams that are large in diameter and/or possess relatively high dust loading, such that the average maximum transmitted laser power is less than 10% of the original laser power.

The direct absorption mode will be discussed first, with reference to FIGS. 5–8. Briefly, the structure in FIGS. 1 through 4 described above operates as follows. The tunable laser source 300 outputs a laser beam which is scanned through a predetermined range of wavelengths. The laser is preferably scanned over a wavenumber range of at least 3 cm$^{-1}$ for maximum accuracy in determining the off-gas temperature. In the preferred embodiment of the direct absorption mode, the laser is scanned over the wavenumber range of 2111 to 2115 cm$^{-1}$. Other wavelength ranges may be used to optimize the sensor performance for characterizing off-gas streams from other steelmaking processes. The laser output power should be at least 100 microwatts to ensure adequate detection sensitivity; however, the laser must lase in only a single mode. When using a lead-salt diode laser source, the laser operating temperature should be between 85 and 110 K to ensure adequate wavelength control while minimizing liquid nitrogen coolant usage.

Electronics module 500 regulates both the laser temperature and the injection current. In the preferred embodiment, the electronics module regulates the injection current so that TDL 310 is scanned over its wavelength tuning range at a frequency of 1000 Hz. The laser beam passes through the off-gas of BOF 100, where certain wavelengths are absorbed by molecular vibration-rotation transitions of CO, $CO_2$, and $H_2O$ molecules in the off-gas. The detector module 400 detects the transmitted laser beam and outputs data to the data processing computer 610. Computer 610 stores previously calculated theoretical transmission spectra and compares characteristics of the detected data, such as laser transmittance and the absorbance ratio of CO and $CO_2$ (defined below), with the calculated transmission spectra to determine measurements of average gas concentration, temperature, and other characteristics as discussed below.

In particular, absorption intensities of individual molecular transitions for CO and $CO_2$ depend on both their concentration and temperature in well-defined relationships. By fitting the measured transmission spectra to theoretical calculations, measurements of average gas concentrations and temperature can be made along the optical line-of-sight. The theoretical calculations are based on the following method:

(1) Absorption wavenumbers ($v_i$) and lower energy levels (E") for individual CO vibrational transitions (for $^{12}C^{16}O$, $^{13}C^{16}O$, $_{12}C^{18}O$, $^{12}C^{17}O$, and $^{13}C^{18}O$ isotopes) are calculated for lower vibrational quantum numbers (v") up to 10 (using the method of R. Farrenq, et al., *J. Mol. Spec.*, 1991, 375; incorporated herein by reference).

(2) These values are then used as input data for the calculation of CO absorbance spectra, where the shape of the calculated CO absorption features are referred to as "Voigt profiles" (using the method of J. H. Pierluissi, et al., *J. Quant. Spectrosc. Radiat. Transfer*, 1977, 555; incorporated herein by reference). Input values in addition to $v_i$ and E" (above), are the CO concentration, $C_{co}$, expressed in partial pressure in units of atmospheres, the path length through the absorbing gas medium, L, the gas temperature, T, in Kelvins, the collisional half-width, $\gamma_i$, for the CO absorption feature at the calculated temperature (determined experimentally in the work of P. L. Varghese and R. K. Hanson, *J. Quant. Spectrosc. Radiat. Transfer*, 1991, 339; incorporated herein by reference), and the line intensity, S, (extracted from the HITRAN data base, HITRAN 1992 Database, Version 2.31, Ontar Corp., 9 Village Way, North Andover, Mass.).

(3) CO absorbance spectra are calculated for temperatures from 1500 to 2100K, at intervals of 50K. The relevant quantity measured is laser transmittance, $T(v)$, which is expressed as the ratio of the incident laser intensity, $I_o$, to the detected laser intensity, $I$, for a given wavenumber, $v$. The resulting transmittance spectrum is directly related to an absorbance spectrum $a(v)$ by $$a(v) = -\log(T(v)).$$

Figure 5:
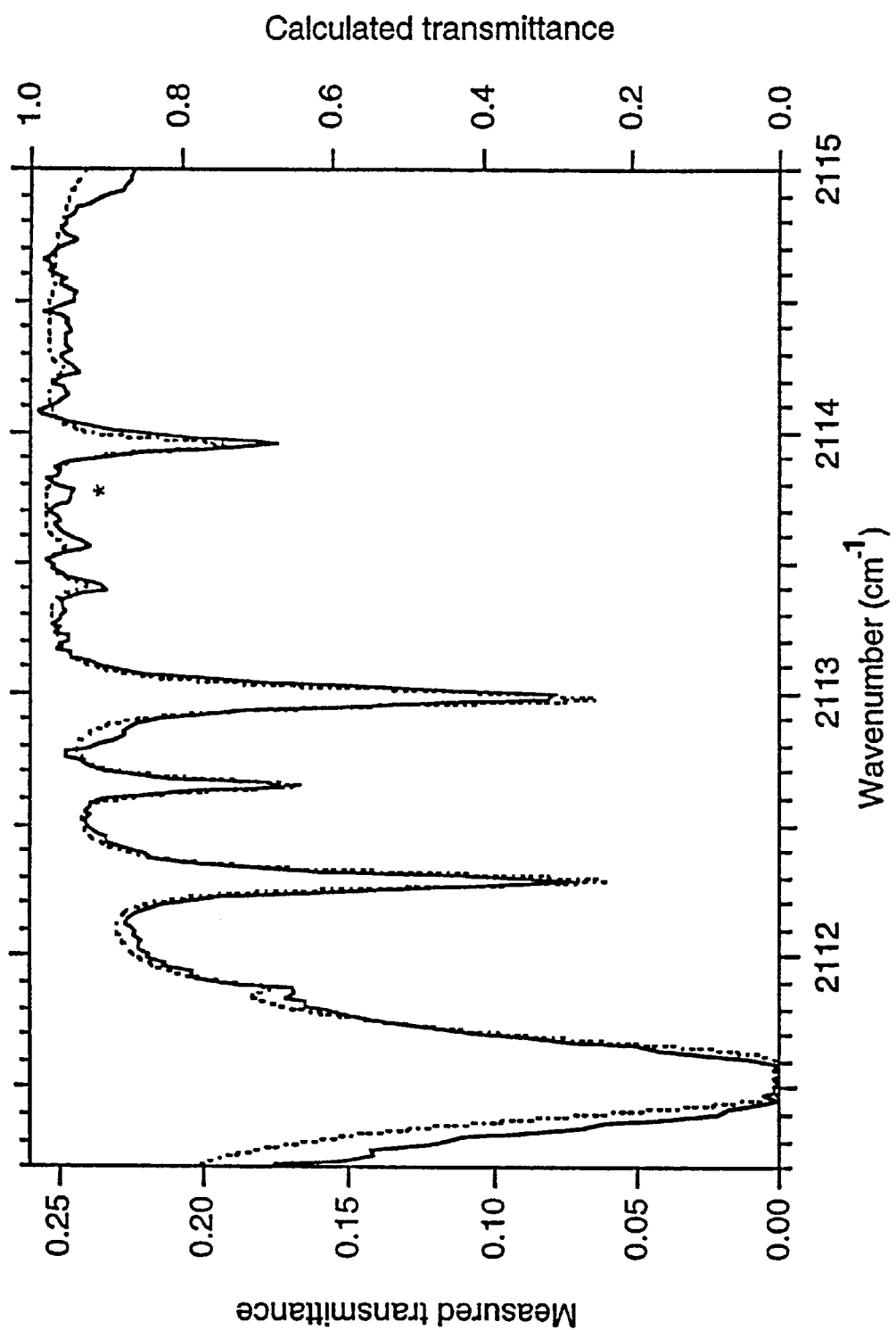
FIG. 5 is a graph showing measured and calculated transmittance values as a function of wavenumber.

FIG. 5 shows data for an example in which measurements were made of a laser beam transmitted above the mouth of a pilot-scale BOF, and compared to a calculated transmittance spectrum. The solid curve shows the transmittance of the laser beam, which indicates the measured CO absorbance via the above relationship. The dotted curve indicates a theoretical calculation of the transmittance characteristics for CO, using a 0.5 m optical path, a 1435 K temperature, a 0.12 atmosphere partial pressure, and 1 atmosphere total pressure. The feature marked with an asterisk in the experimental transmittance is a prominent $CO_2$ absorption that is not reproduced in the CO calculation.

(4) Using the series of calculated CO absorption spectra, the CO absorption lines that are the most sensitive to temperature are identified (for instance, the features at 2112.6 cm$^{-1}$ ($v_i$) and 2113.0 cm$^{-1}$ ($v_j$) in FIG. 5), and ratios of absorbance $R_T$ as a function of temperature are computed:

$$R_T = a(v_i)/a(v_j)$$

(5) A 9th-degree polynomial is then fit to these various ratios RT (using known curve fitting techniques) to generate a mathematical function expressing absorption ratios for the two chosen CO absorption features over the entire (1500 to 2100 K) temperature range.

Using this method, gas temperatures can be computed in real time for optical sensor signals. Transmittance data as a function of wavenumber (as shown in FIG. 5) are generated every second or so, and the magnitude of the transmittance at specific wavenumbers is extracted. The transmittance is rapidly converted to values of absorbance by computer 610 using the relationship noted above. The ratio of absorbance for the chosen absorption features is then used as input to the polynomial fit for $R_T$, and the resulting value of temperature is displayed by the computer and stored in memory. Note also, that since absorbance is directly proportional to the concentration of CO along the optical path length, the partial pressure of CO can also be extracted from this calculation in real time.

Figure 6:
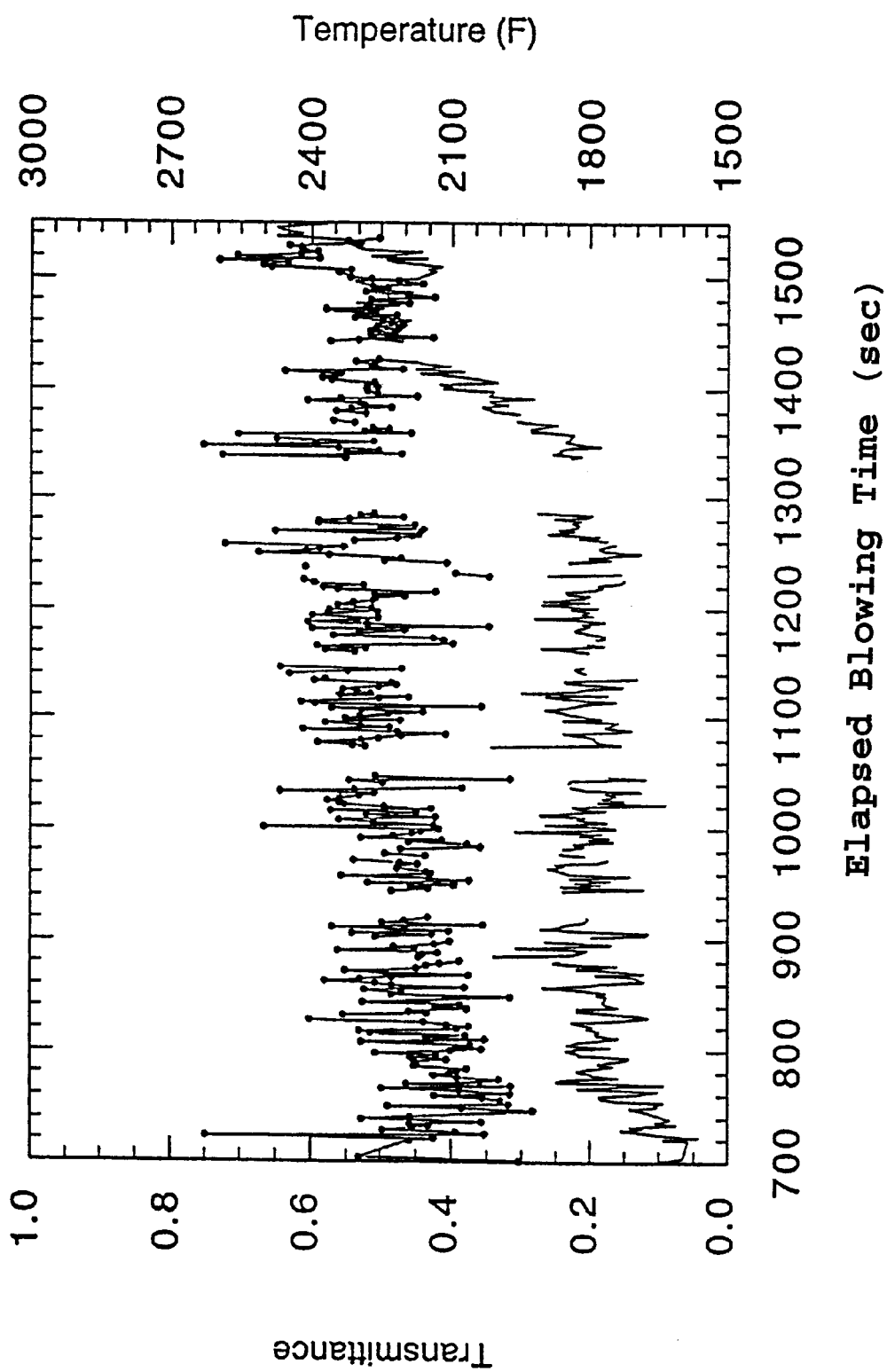
FIG. 6 is a graph showing laser transmittance and temperature values as a function of elapsed blowing time.

FIG. 6 shows a graph of temperature and laser transmittance as a function of time throughout a heat. The temperature (upper curve) is calculated as just described. The laser transmittance shown in FIG. 6 (lower curve) is the value of peak transmittance at a wavenumber of 2114.1 cm$^{-1}$. The maximum laser transmittance through the off-gas stream is related to scattering caused by the large number of particles entrained in the off-gas, as well as the concentration of infrared-absorbing gases along the optical line-of-sight. At 2114.1 cm$^{-1}$, little CO and $CO_2$ molecular absorption is expected, and the reported laser transmittance represents primarily attenuation of the laser beam due to scattering by dust particles. A substantial increase in laser transmittance is observed beginning at about 1300 seconds $O_2$-blowing time, as measured during pilot-scale experiments.

Several gaps in the data shown in FIG. 6 occurred when a sensor lance was lowered into the furnace for extraction of metal samples during oxygen blowing in the 2-ton research BOF. The sensor lance, when lowered, effectively blocked the infrared laser beam for approximately 20 seconds during each sample extraction. This situation does not occur in a standard commercial BOF.

At the present time, this method for the real-time measurement of gas temperature and concentration cannot be used for carbon dioxide (the small absorption features in FIG. 5 that are not fit in the calculated transmittance spectrum [dashed curve], the most prominent of which is marked by an asterisk). The primary obstacle in implementing this method for steelmaking is the lack of fundamental data for $CO_2$ absorption transitions as a function of temperature, at the high temperatures of interest, to be used in the calculations described above.

Figure 7:
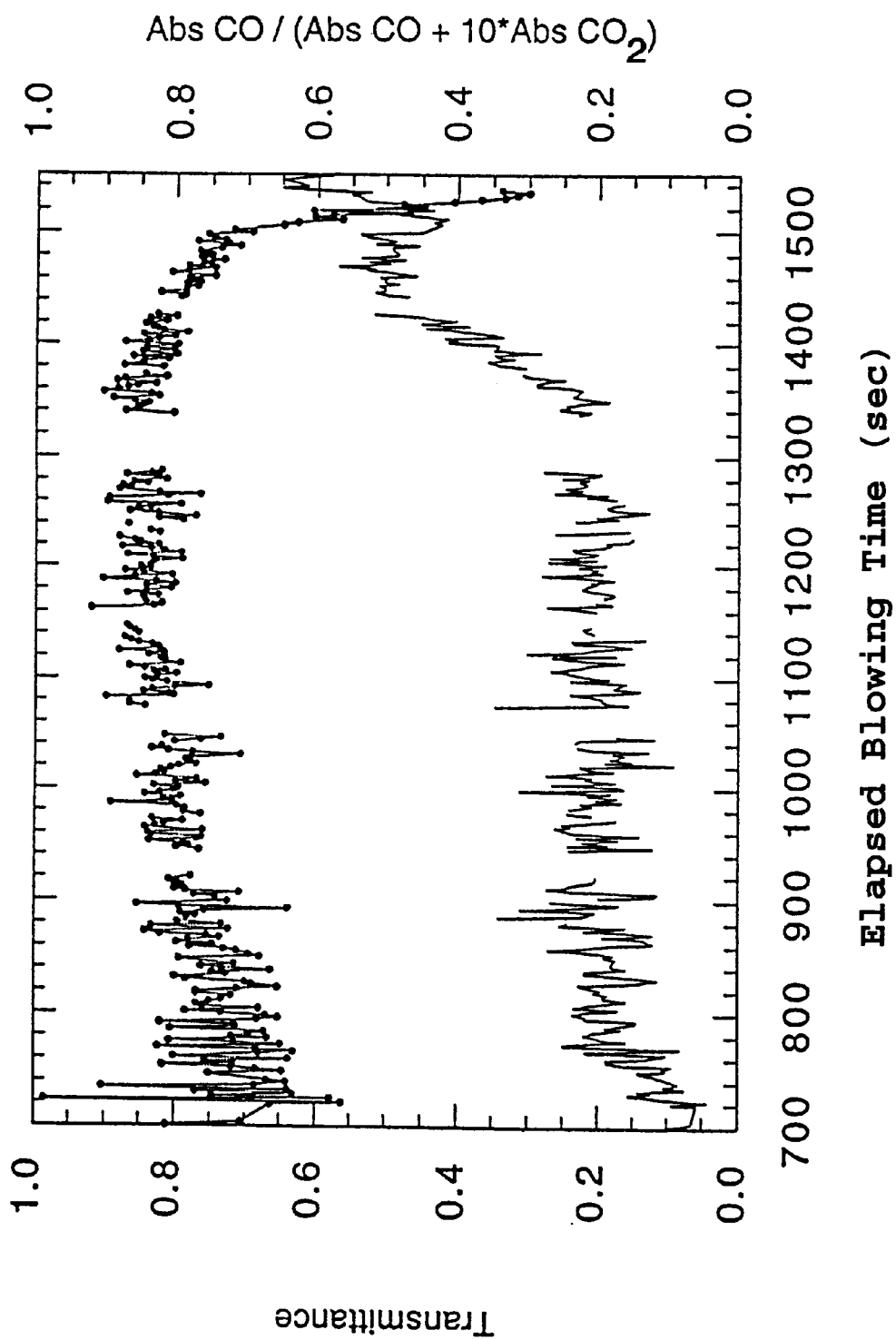
FIG. 7 is a graph showing laser transmittance and absorbance ratio values as a function of elapsed blowing time.

However, much can be learned about the relative concentrations of CO and $CO_2$ by simply tracking a ratio of absorption intensities for absorption lines of the two gases throughout oxygen blowing. The ratio function used is:

$$R_{Abs} = Abs_{CO}/(Abs_{CO} + c*[Abs_{CO2}])$$

where $Abs_{CO}$ and $Abs_{CO2}$ are the real time absorbance values of CO and $CO_2$ absorption features at 2112.6 and 2113.8 cm$^{-1}$, respectively (see FIG. 5), and c is a constant whose value is selected so that the ratio $R_{Abs}$ of CO and $CO_2$ absorbance values is approximately equal to the ratio of CO and $CO_2$ concentrations observed experimentally. FIG. 7 shows a graph of the laser transmittance signal (lower curve, repeated from FIG. 6) and the function $R_{Abs}$ during a heat (i.e., plotted as a function of elapsed blowing time). In this illustration the constant "c" is chosen to equal 10, thus yielding a value for $R_{Abs}$ of approximately 0.8 (which is similar to the ratio of $CO/CO_2$ concentrations observed experimentally) during most of the oxygen blow, as shown in FIG. 7 (top curve). The value of the ratio function begins to drop at about 1350 seconds in this graph, and rapidly decreases at about 1500 seconds.

Analysis of metal samples extracted during blowing (again, causing the several gaps in the data shown in FIGS. 6 and 7) show that the initial drop in $R_{Abs}$ and the rise in maximum laser transmittance occur for a carbon content of 0.7%. Significant changes in these two measured optical properties continue down to a carbon content of the melt of 0.03%. Computer 610 can calculate and display $R_{Abs}$ and the initial drop can be used to indicate that the carbon content has reached about 0.7%.

During pilot-scale experiments, measured values of gas temperature and the behavior of both maximum laser transmittance and $R_{Abs}$ were sufficiently repeatable over about 10 heats to show that this method can be used to extract real-time values of gas temperature, relative $CO/CO_2$ concentration, and end-point melt carbon values for applications for which the maximum laser transmittance is greater than 0.1.

Figure 8:
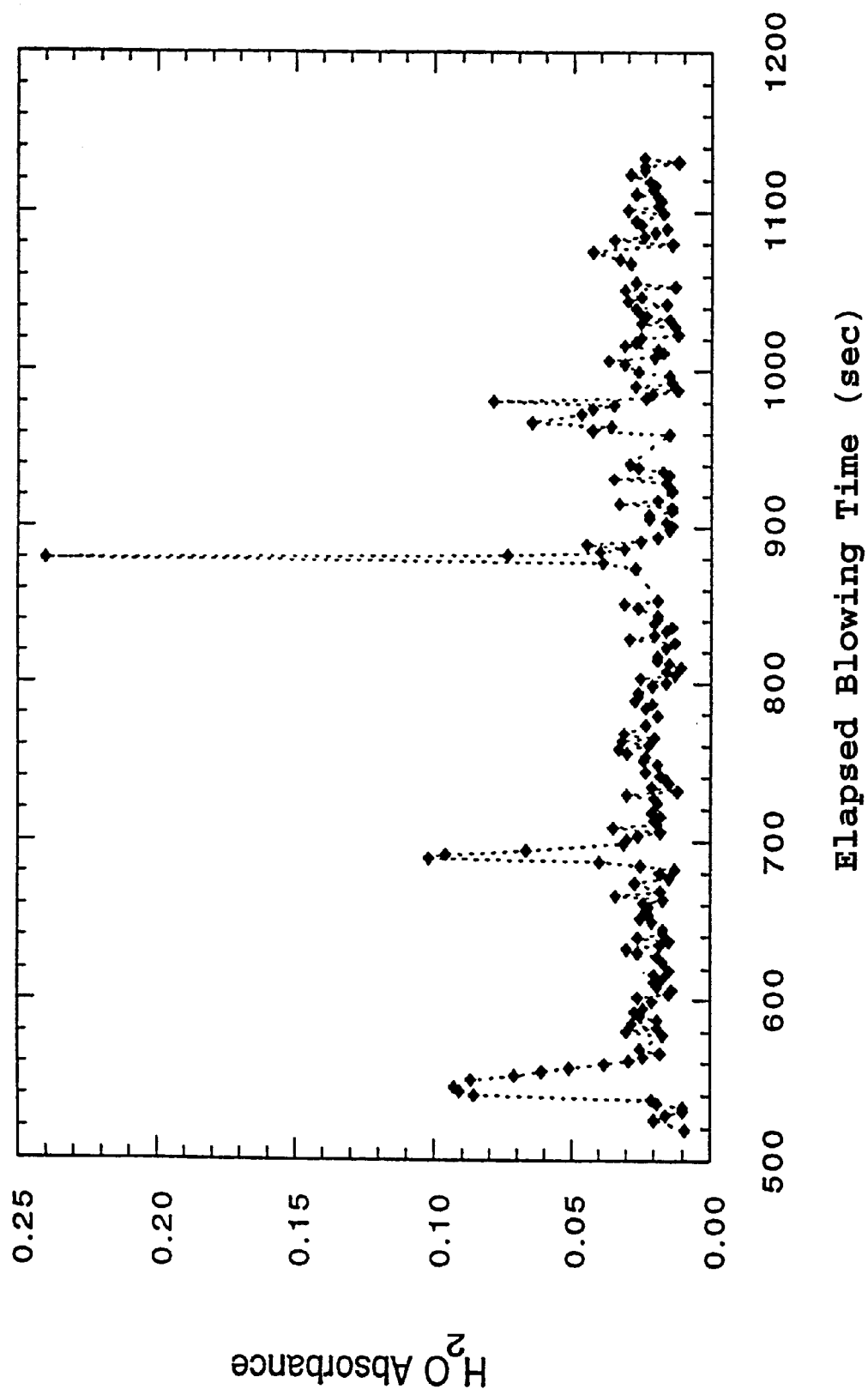
FIG. 8 is a graph showing $H_2O$ absorbance as a function of elapsed blowing time.

The presence of hydrogen is detected by monitoring transmission spectra corresponding to water absorption lines, e.g., features at a wavenumber of 2114.5 cm$^{-1}$. FIG. 8 shows a graph of water absorbance as a function of elapsed blowing time. Transients can be clearly seen where the absorbance suddenly increases (i.e., the transmittance at these spectra decreases), indicating high levels of water vapor. During normal steelmaking procedures in a pilot-scale BOF, water absorption lines were observed only briefly when flux was added to the melt early in the oxygen blowing sequence and during the extraction of metal samples for analysis by a sampling lance. Water vapor can also be detected in the off-gas during preheating periods (not shown in FIG. 8). Preheating of the furnace refractory lining is performed by blowing oxygen to combust coal and/or charcoal, and strong water line absorptions are observed continuously under these conditions. Absorption peaks at other times indicate an abnormal high level of water vapor, and computer 610 can monitor the signal level at 2114.5 cm$^{-1}$ so that detection of a water vapor level above a certain threshold can be used to trigger an alarm or signal to an operator that potentially dangerous levels of hydrogen gas may be present. This is only an indirect indication of the presence of hydrogen, since it is H$_2$O rather than hydrogen per se that is detected. However, because the monitoring is done in the actual off-gas, this monitoring method is more reliable than the conventional method of monitoring the flow into and out of a water-cooled lance or exhaust duct for water leakage that could be a source of excess hydrogen.

The preferred embodiment of the harmonic detection mode of operation will be described with respect to FIGS. 9–13. Only the aspects that differ from the direct absorption mode will be discussed in detail.

In this mode, the TDL beam is wavelength-modulated by rapidly varying the injection current with a 50 KHz sinusoidal waveform as the laser is scanned over its wavelength tuning range. In the preferred embodiment of this mode, the laser beam wavelength is scanned over a wavenumber range of about 2090 to 2093 cm$^{-1}$. The second harmonic of the transmitted laser signal at the detector is then detected using lock-in amplifier 620 at 100 KHz. This method has been demonstrated to allow detection of TDL beams that have been attenuated by five orders of magnitude from their initial intensity. The precise frequencies of laser tuning and wavelength modulation are not critical (high-frequency wavelength modulation of up to several gigahertz is possible). The ratio between the frequency of scanning the laser over its tunable range and the frequency of wavelength modulation preferably should be at least 1:1,000.

In the discussion below of determining the off-gas characteristics in the harmonic detection mode, the examples given are for a full-scale commercial basic oxygen furnace, and wavelength modulated signals are demodulated at the second harmonic frequency using a lock-in amplifier. The resulting waveforms resemble a mathematical second-derivative of the transmission spectrum with negative-going absorption peaks. For convenience, these measured and calculated second-harmonic signals are referred to as "2f" signals.

Calculated 2f signals are produced using a software algorithm (to be described below) that transforms either calculated or experimental direct absorption spectra into the corresponding second harmonic ("2f") spectra. The input spectra may be either normalized transmittance spectra, or non-normalized sensor signals. This algorithm may also be used to produce first harmonic ("1f") or other higher harmonic spectra if so desired. This approach is necessary for the quantitative interpretation of harmonic spectra in terms of off-gas temperature and composition, since the measured 2f spectra cannot easily be "inverted" to simple transmission spectra which are easily interpreted. Previous investigations (notably, J. Reid and D. Labrie, *Appl. Phys. B,* 1981, 203; incorporated herein by reference) have shown that existing inversion procedures are only successful for gas media that are very nearly transparent, and are inappropriate for the present application.

The present approach is similar to that followed in the direct absorption method described above. It allows us to construct calculated 2f spectra for a series of off-gas temperatures and concentrations. ago Spectral features that are most sensitive to these variables for a given laser wavelength tuning range are then selected, and a functional fit of, for instance, the intensity ratio of two 2f absorption lines for CO is derived and is used to fit the experimentally observed sensor data to produce real-time values of off-gas temperature. Absorption lineshape information, including peak width and wavenumber position, may also be used for this purpose.

The software algorithm for transformation of transmittance spectra to 2f spectra simulates the action of a lock-in amplifier upon the electrical output of the detector module signal and performs the following operations. An input transmittance spectrum (either calculated according to the direct absorption method described above, or experimentally measured) is expanded by interpolating additional data points using cubic-spline fitting. Since the scanning of the laser through its wavenumber tuning range is linear with respect to time, the resulting expanded transmittance spectrum is represented as transmission intensity with respect to time. In this representation, at least ten data points are present for each cycle of the highfrequency harmonic to be evaluated (100 KHz for the second harmonic, in the present example).

The intensities of the expanded transmission spectrum are then redistributed in time to represent the action of a sinusoidal modulation of the laser wavenumber by high-frequency modulation as it is scanned through its wavenumber tuning range. The maximum amplitude of the sinusoidal redistribution is equal to the experimental modulation amplitude, while the frequency of the sinusoidal redistribution is equal to the experimental value of 50 KHz.

The mathematically expanded and "modulated" transmission spectrum is then multiplied by a sine wave at the experimental lock-in amplifier frequency, in this case, the second harmonic frequency at 100 KHz. The resulting function is then mathematically filtered with a low-pass function. The additional data points used to expand the original transmittance spectrum are removed to simplify digital comparison with experimental data, and the result is a mathematical 2f spectrum that is essentially identical with experimentally measured data.

Figure 9A:
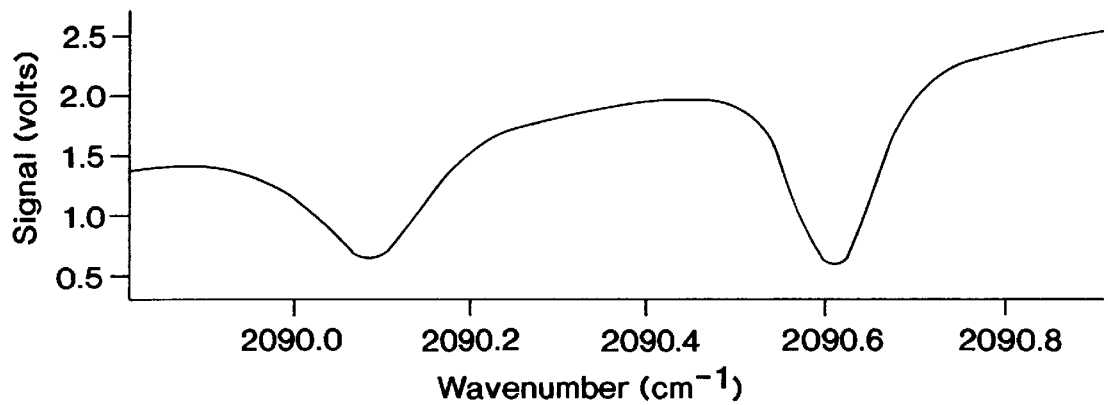
FIG. 9a is a graph of an experimentally measured direct absorption spectrum of CO and water vapor in the laboratory.
Figure 9B:
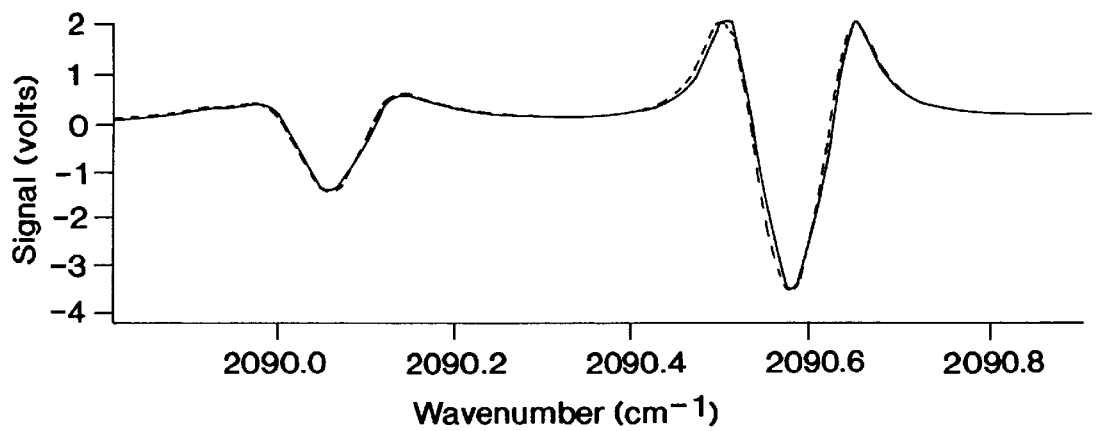

An example is shown in FIGS. 9a and 9b. FIG. 9a shows an experimental, non-normalized direct absorption spectrum of carbon monoxide and water vapor obtained in the laboratory with the off-gas sensor configuration described above with reference to FIGS. 1 to 4. FIG. 9b shows the measured 2f spectrum (solid curve) and a calculated 2f spectrum (dashed curve) calculated using the algorithm described above from the direct absorption spectrum of FIG. 9a. The measured and calculated 2f spectra of FIG. 9b show excellent agreement.

FIG. 10a shows a calculated transmission spectrum for CO at 0.5-atm partial pressure, 3.65-m path length, and 1900 K (2960° F.). FIG. 10b shows (as a dashed curve) a 2f spectrum calculated from the spectrum of FIG. 10a. FIG. 10b also shows (as a solid curve) an experimental 2f spectrum measured in a full-scale BOF during oxygen blowing. A comparison of the two curves in FIG. 10b shows good agreement of both position, shape, and relative intensities of the various absorption features in the measured and calculated 2f signals, even without including the contribution of CO$_2$ in the calculated 2f spectrum. The feature at 2091.55 cm$^{-1}$ (labeled "a") is a CO absorption line that is particularly sensitive to temperature, while the CO feature at 2091.92 cm$^{-1}$ (labelled "b") is reasonably constant with varying temperature. The ratio of these two intensities can be used to track the off-gas temperature throughout the oxygen blow, as illustrated in FIG. 11.

Figure 11:
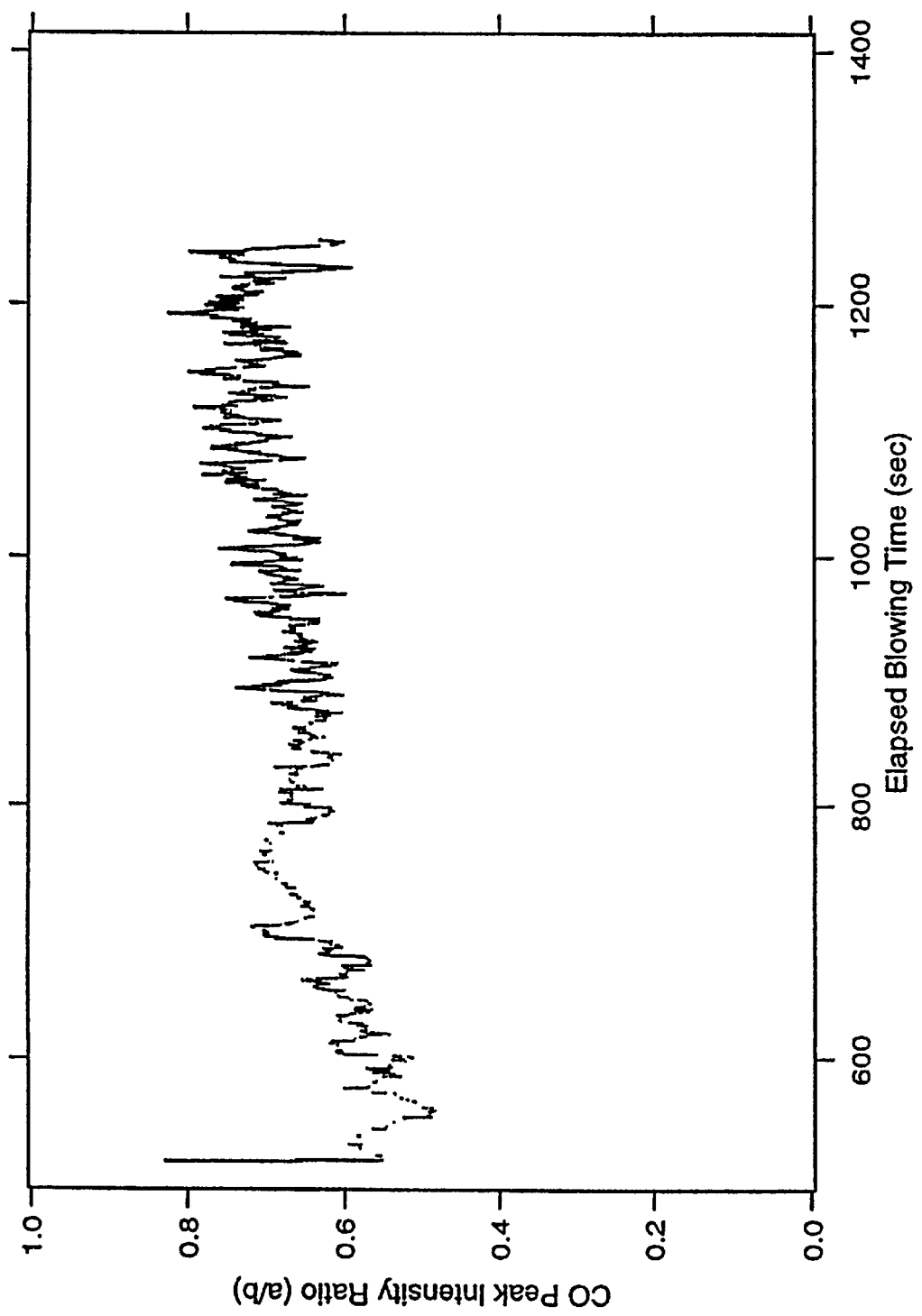
FIG. 11 is a graph showing carbon monoxide peak intensity ratio values as a function of elapsed blowing time.

FIG. 11 shows a graph of the ratio of intensities of features a and b in FIG. 10b. The ratio of intensities of these features in the calculated 2f spectra of FIG. 10b have also been computed, and these intensity ratios were found to be substantially linear with respect to temperature over the range of 0.5 to 0.9, which corresponds to a temperature range of about 1750 K to about 1900 K. The ratios of experimental intensities plotted in FIG. 11 can be converted to corresponding temperatures based on this linear relationship, e.g., a value of 0.7 corresponds to a temperature of about 1825 K.

The relative concentrations of CO and $CO_2$ are determined using the features labelled "a" and "c" in FIG. 10b. Most of the strong absorption features shown in FIG. 10b are due to carbon monoxide. However, the shoulder-like feature labelled "c" in the experimental curve of FIG. 10 at 2092.23 $cm^{-1}$ is due to $CO_2$ in the off-gas. The intensities of the CO and $CO_2$ features (labelled "a" and "c" respectively) are denoted $I_{CO}$ and $I_{CO2}$, respectively, and are combined in the function:

$$Ratio = I_{CO}/(I_{CO} + [k * I_{CO2}]),$$

where "k" is an arbitrary constant used to produce a ratio similar to experimentally observed results, as in the equation for $R_{Abs}$ above.

Figure 12:
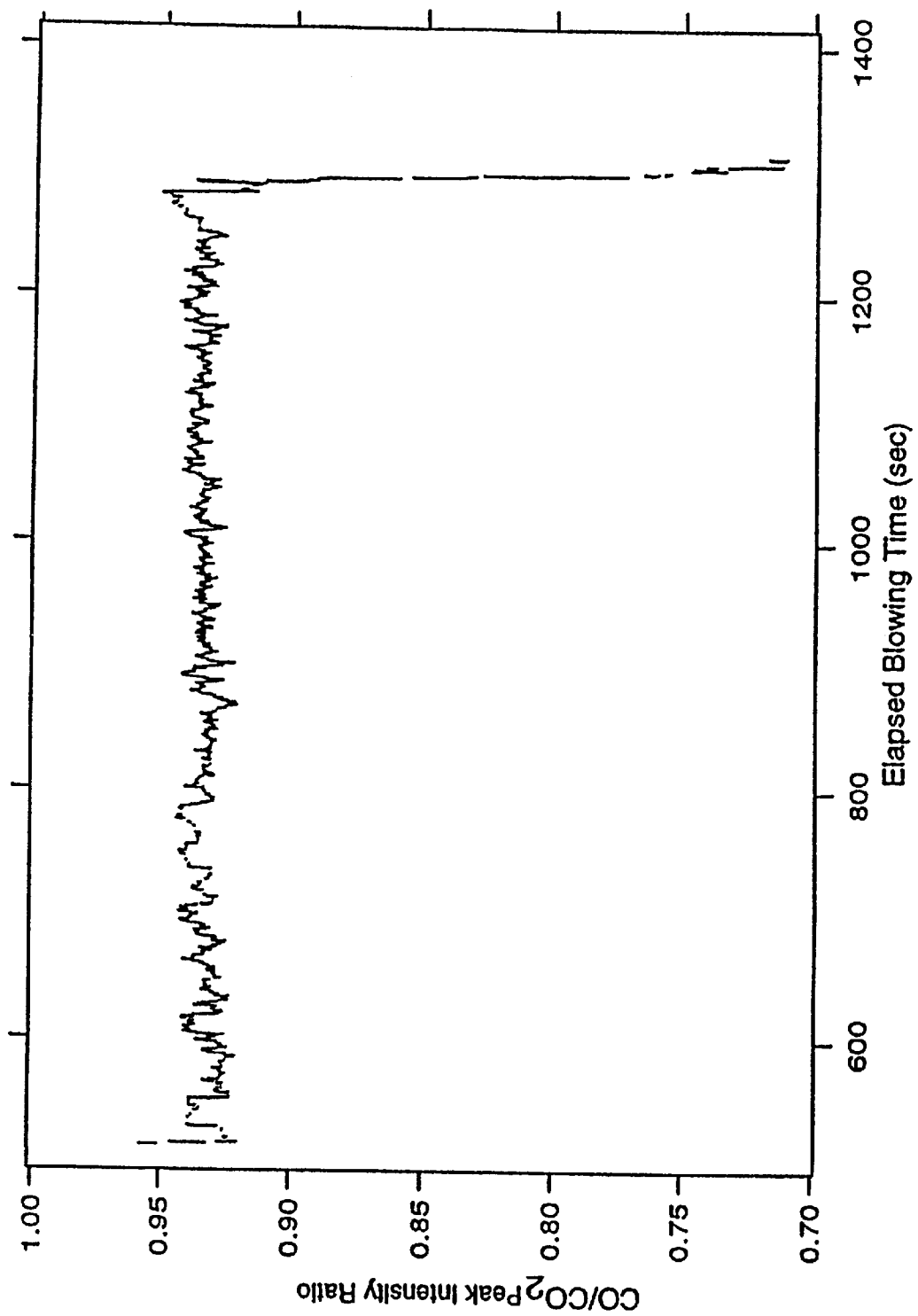
FIG. 12 is a graph showing the ratio of carbon monoxide and carbon dioxide peak intensity values as a function of elapsed blowing time.

FIG. 12 shows a graph of this intensity ratio, which is used to track the relative concentrations of CO and $CO_2$ throughout the oxygen blow. The graph of FIG. 12 corresponds to the heat illustrated by the graph of FIG. 11, using a value of k=0.1. As shown in FIG. 12, the $CO/CO_2$ ratio is very stable throughout most of the blow. As the melt approaches the final stages tz of decarburization, however, the CO in the off-gas is directly oxidized to $CO_2$. At this point, the value of the ratio function drops rapidly (as shown in FIG. 12 beginning at about 1250 seconds of elapsed blowing time). The values of the ratio functions for various CO and $CO_2$ absorption features may be useful in determining final melt carbon content in real-time for applications where continuous sensor data may be obtained during the final melt decarburization stage.

Figure 13:
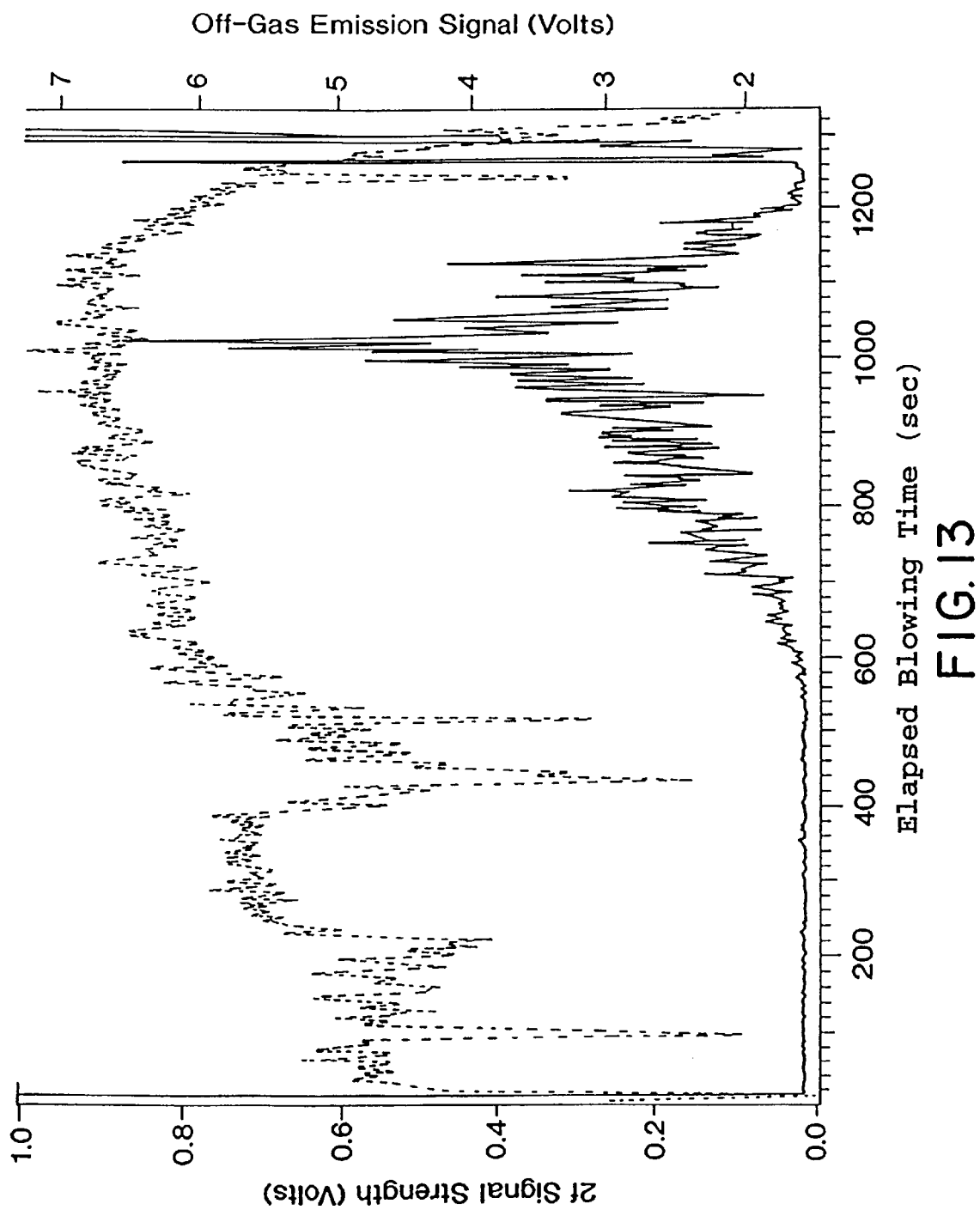
FIG. 13 is a graph showing the off-gas emission intensity signal (upper curve) and the 2f signal strength (lower curve) as a function of elapsed blowing time.

For some TDL tuning regions in the 1700–2500 $cm^{-1}$ (4.00–5.88 μm) range, this method of determining end-point carbon content does not work as well. This is principally due to the very large increase in $CO_2$ absorbance at the end of the oxygen blow, and a very large attenuation of the laser beam through the off-gas. In this case, a second approach may be used to monitor end-point carbon content. "2f" spectra are recorded as a function of wavenumber (as in FIG. 10b, solid curve) every second or so, and the average absolute value of the 2f spectra (referred to below as "2f signal strength") is calculated by computer 610 for each spectrum. This 2f signal strength is displayed by computer 610 and stored in memory throughout an oxygen blow. The time behavior of the 2f signal strength exhibits a characteristic and repeatable response with respect to blowing time and accumulated oxygen. FIG 13 shows the 2f signal strength (lower curve) as a function of $O_2$-blowing time for a heat in a full-scale BOF (this is a different heat than that illustrated in FIGS. 11 and 12). For most heats, the 2f signal strength goes to zero during the final stage of melt decarburization. Furthermore, for some heats with very low final melt carbon concentrations, the 2f signal strength becomes non-zero before the end of oxygen blowing, due to a resulting decrease in $CO_2$ concentration. Furthermore, the time of disappearance and reappearance of the 2f signal strength near the end of oxygen blowing appears to be correlated with laser wavelength, such that longer wavelengths (lower wavenumbers) result in shorter periods when the 2f signal strength is zero. The characteristics of these 2f signal strength curves may be useful in tailoring the off-gas sensor to the measurement of specific melt carbon contents for specific steelmaking processes, and is under further investigation.

The total emission falling on the detector 450 through the narrow-band optical filters 480a and 480b shows no spectral features across the laser tuning range of 3 $cm^{-1}$. The off-gas emission intensity signal is evaluated for a single laser scan by taking multiple samples of the electrical output signal of detector 450 and amplifier 490 before the signal is routed through lock-in amplifier 620. The multiple samples are then averaged by computer 610 in real time, and the result is displayed and stored in memory throughout an oxygen blow. An example of such a display is shown in FIG. 13 (upper curve). The rapid decrease in off-gas emission, beginning at about 1100 seconds of elapsed blowing time, can be correlated with melt carbon content between 0.06 and 0.03 wt %. Thus, an estimate that the carbon content is in this range can be made from the detector signal even when the more broadly-applicable technique using the intensity ratio cannot be used.

The combination of the 2f signal strength and the total emission methods may be used to produce even more precisely correlated measurements of final melt carbon content due to the independent nature of these two measurements.

Additional information related to the ejection of liquid slag (i.e., "slopping") from the furnace can be extracted from the off-gas emission signal shown in FIG. 13. The sharp decrease in emission intensity (upper curve) between 400 and 600 seconds of elapsed blowing time is well correlated with furnace slopping. The decrease is caused by ejection of slag particles through the sensor's field of view. The rapid changes in signal intensity can be detected by computer 610 and used to alert the furnace operator (or provide a signal to a process controller) that furnace slopping is imminent, or is in progress. The position of the oxygen lance and/or the oxygen flow rate can then be adjusted (either manually or automatically) to prevent or stop slopping.

Although a specific embodiment of the invention has been described, the invention is not limited to this embodiment. For example, the wavelength ranges need not be identical to those used in the preferred embodiments. Rather, any range that includes characteristic lines of interest may be used, and those of ordinary skill will appreciate that the technique of the invention can be adapted to analyze features other than CO, $CO_2$, and $H_2O$ concentrations. It will also be appreciated that a different range may be required to give optimal results in adapting the invention to a different steelmaking process than the BOF described in the preferred embodiment. Further, the invention is not limited to a tunable diode laser and an InSb detector. Instead, any radiation source that can be scanned through the desired range of wavelengths at a power level sufficient for detection may be used, and any detector of a material suitable to detect the transmitted beam can be used. In this regard, it should also be understood that the precise arrangement of mirrors, lenses, and other components in the laser source module and detector module are not necessary. Other arrangements can be used that perform the same functions of guiding and focusing a laser beam and blocking and filtering unwanted components from the detector.

Accordingly, those skilled in the art will appreciate that, while the present invention has been described with respect to the structure and operation of a preferred embodiment, the invention is not limited to the specific structure and operation discussed above. To the contrary, there are numerous variations of the disclosed embodiment that can be made by those of ordinary skill without departing from the spirit and scope of the present invention. Therefore, the invention should be construed to include these variations and all others encompassed within the scope of the invention as set forth in the appended claims.

What is claimed is:

1. An apparatus for non-intrusive collection of off-gas data in a steelmaking furnace, comprising:

transmitting means for transmitting a laser beam through the off-gas produced by the steelmaking furnace, said transmitting means having a tuning range of laser beam wavelengths;

controlling means for controlling said transmitting means to repeatedly scan the laser beam through a pre-set continuous range of wavelengths in its tuning range; and detecting means for detecting the laser beam transmitted through the off-gas and for converting the detected laser beam to an electrical signal.

2. An apparatus according to claim 1, wherein said controlling means comprises means for performing wavelength modulation of the laser beam while scanning the laser beam through a plurality of wavelengths in its tuning range, and wherein said detecting means comprises a phase-sensitive device for detecting a harmonic of the wavelength-modulated laser beam transmitted through the off-gas.

3. A non-intrusive method for collecting off-gas data in a steelmaking furnace, comprising the steps of:

transmitting a laser beam through the off-gas produced by the steelmaking furnace using a laser having a tuning range of laser beam wavelengths;

repeatedly scanning the laser beam through a pre-set continuous range of wavelengths in its tuning range;

detecting the laser beam transmitted through the off-gas; and converting the detected laser beam to an electrical signal.

4. A method according to claim 3, wherein said step of repeatedly scanning the laser beam comprises a step of performing wavelength modulation of the laser beam while scanning the laser beam through a plurality of wavelengths in its tuning range, and wherein said detecting step comprises a step of detecting a harmonic of the wavelength-modulated laser beam transmitted through the off-gas.

5. An apparatus for monitoring characteristics of off-gas in a steelmaking furnace, comprising:

transmitting means for transmitting a laser beam through the off-gas produced by the steelmaking furnace, the laser beam being repeatedly scanned through a pre-set continuous range of wavelengths during transmission;

detecting means for detecting the transmitted laser beam and for generating an electrical signal corresponding to the detected laser beam; and processing means for processing the electrical signal to determine at least one characteristic of the off-gas in the steelmaking furnace.

6. An apparatus according to claim 5, wherein said processing means comprises means for storing calculated theoretical characteristics of the off-gas and means for comparing the electrical signal to the calculated characteristics to determine at least one measured characteristic of the off-gas.

7. An apparatus according to claim 5, wherein said processing means comprises means for extracting information of one or more preselected wavelengths from the electrical signal and means for determining at least one characteristic of the off-gas based on the extracted information.

8. An apparatus according to claim 7, wherein said processing means comprises means for determining ratio values using absorbance values for two wavelengths and for using the ratio values with a polynomial determined from theoretical spectra calculations to determine a temperature value.

9. An apparatus according to claim 5, wherein said transmitting means comprises means for performing wavelength modulation of the transmitted laser beam while scanning the laser beam through the range of wavelengths, and wherein said detecting means comprises means for detecting a harmonic of the modulated laser beam.

10. An apparatus according to claim 9, wherein said processing means comprises means for extracting intensity information regarding at least two preselected wavelengths from the electrical signal and means for determining at least one characteristic of the off-gas based on a ratio of the intensity information for one or more pairs of preselected wavelengths.

11. An apparatus according to claim 9, wherein said detecting means comprises a detector and said processing means comprises means for determining the total emission intensity incident on said detector and means for determining at least one characteristic of the off-gas based on the determined emission intensity.

12. An apparatus according to claim 9, wherein said processing means comprises means for calculating an average 2f signal strength and determining means for determining at least one characteristic of the off-gas using the calculated average 2f signal strength.

13. An apparatus according to claim 12, wherein said processing means further comprises means for determining the total emission intensity incident on said detector, and wherein said determining means uses both the calculated average 2f signal strength and the total emission intensity to determine at least one off-gas characteristic.

14. A method for monitoring characteristics of off-gas in a steelmaking furnace, comprising the steps of:

transmitting a laser beam through the off-gas produced by the steelmaking furnace, the laser beam being repeatedly scanned through a pre-set continuous range of wavelengths during transmission;

detecting the transmitted laser beam;

generating an electrical signal corresponding to the detected laser beam; and processing the electrical signal to determine at least one characteristic of the off-gas in the steelmaking furnace.

15. A method according to claim 14, wherein said processing step comprises the step of comparing stored calculated theoretical characteristics of the off-gas to the electrical signal to determine at least one measured characteristic of the off-gas.

16. A method according to claim 14, wherein said processing step comprises the step of extracting information of one or more preselected wavelengths from the electrical signal and determining at least one characteristic of the off-gas based on the extracted information.

17. A method according to claim 16, wherein said processing step further comprises the steps of determining ratio values using absorbance values for two wavelengths and using the ratio values with a polynomial determined from theoretical spectra calculations to determine a temperature value.

18. A method according to claim 14, wherein said transmitting step comprises the step of performing wavelength modulation of the transmitted laser beam while scanning the laser beam through the range of wavelengths, and said detecting step comprises the step of detecting a harmonic of the modulated laser beam.

19. A method according to claim 18, wherein said processing step comprises the step of extracting intensity information of at least two preselected wavelengths from the electrical signal and determining at least one characteristic of the off-gas based on a ratio of the intensity information for one or more pairs of preselected wavelengths.

20. A method according to claim 18, wherein said processing step comprises the step of determining the total emission intensity incident on a detector and determining at least one characteristic of the off-gas based on the determined emission intensity.

21. A method according to claim 18, wherein said processing step comprises the steps of calculating an average 2f signal strength and determining at least one characteristic of the off-gas using the calculated average 2f signal strength.

22. A method according to claim 21, wherein said processing step further comprises the step of determining the total emission intensity incident on a detector and wherein said determining step comprises the step of determining at least one characteristic of the off-gas using both the calculated average 2f signal strength and the total emission intensity.

23. An apparatus for non-intrusive collection of off-gas data in a steelmaking furnace, comprising:
  a tunable diode laser arranged to transmit a laser beam through the off-gas produced by the steelmaking furnace;
  a control circuit electrically connected to said tunable diode laser to provide an injection current to said tunable diode laser, said control circuit varying the injection current provided to said tunable diode laser so that said tunable diode laser outputs a laser beam that repeatedly scans through a pre-set continuous range of wavelengths; and
  a detector that receives the laser beam and generates an electrical signal corresponding to the received laser beam.

24. An apparatus according to claim 23, further comprising a computer, said computer receiving the electrical signal and processing the electrical signal to determine at least one characteristic of the off-gas.

25. An apparatus according to claim 23, wherein said control circuit varies the injection current to wavelength modulate the laser beam while scanning the laser beam through the plurality of wavelengths, and wherein said detector comprises a lock-in amplifier for detecting a harmonic signal of the modulated laser beam.

26. An apparatus according to claim 25, further comprising a computer, said computer receiving the electrical signal and processing the electrical signal to determine at least one characteristic of the off-gas.

27. An apparatus according to claim 5, wherein the pre-set continuous range of wavelengths is a range of at least about 2 cm$^{-1}$.

28. An apparatus according to claim 27, wherein the pre-set continuous range of wavelengths is one of (i) a wavenumber range of about 2111 to 2115 cm$^{-1}$ and (ii) a wavenumber range of about 2090 to 2093 cm$^{-1}$.

29. A method according to claim 14, wherein the pre-set continuous range of wavelengths is a range of at least about 2 cm$^{-1}$.

30. A method according to claim 29, wherein the pre-set continuous range of wavelengths is one of (i) a wavenumber range of about 2111 to 2115 cm$^{-1}$ and (ii) a wavenumber range of about 2090 to 2093 cm$^{-1}$.

31. An apparatus according to claim 23, wherein the pre-set continuous range of wavelengths is a range of at least about 2 cm$^{-1}$.

32. An apparatus according to claim 31, wherein the pre-set continuous range of wavelengths is one of (i) a wavenumber range of about 2111 to 2115 cm$^{-1}$ and (ii) a wavenumber range of about 2090 to 2093 cm$^{-1}$.

* * * * *